United States Patent
He et al.

(10) Patent No.: US 11,287,373 B2
(45) Date of Patent: Mar. 29, 2022

(54) METHOD AND SYSTEM FOR IN-SITU DETECTION OF CADMIUM CHELATES IN PLANTS

(71) Applicant: Zhejiang University, Hangzhou (CN)

(72) Inventors: Yong He, Hangzhou (CN); Yinglei Zhao, Hangzhou (CN); Pengcheng Nie, Hangzhou (CN); Lei Lin, Hangzhou (CN); Xuping Feng, Hangzhou (CN)

(*) Notice: Subject to any disclaimer, the term of this patent is extended or adjusted under 35 U.S.C. 154(b) by 0 days.

(21) Appl. No.: 17/189,966

(22) Filed: Mar. 2, 2021

(65) Prior Publication Data

US 2022/0034801 A1 Feb. 3, 2022

(51) Int. Cl.
*G01N 21/35* (2014.01)
*G01N 21/3586* (2014.01)
*G01N 15/08* (2006.01)
*G01N 21/3563* (2014.01)

(52) U.S. Cl.
CPC ......... *G01N 21/3586* (2013.01); *G01N 15/08* (2013.01); *G01N 21/3563* (2013.01)

(58) Field of Classification Search
CPC . G01N 21/3586; G01N 15/08; G01N 21/3563
See application file for complete search history.

(56) References Cited

U.S. PATENT DOCUMENTS

2020/0114164 A1* 4/2020 Bourke, Jr. ............ A61N 5/10

* cited by examiner

*Primary Examiner* — Hugh Maupin (57) ABSTRACT

The present disclosure relates to a method and system for the in-situ detection of cadmium chelates in a plant. The method includes: preparing cadmium chloride and phytochelatin (PC) 2 samples with different concentrations; using terahertz time-domain spectroscopy (THz-TDS) to determine a terahertz (THz) reflection image for the cadmium chloride and PC 2 samples; building a cadmium chloride content detection model according to first spectral data; building a PC 2 content detection model according to second spectral data; determining an optimal mixed sample according to the cadmium chloride content detection model and the PC 2 content detection model; building a Cd—$PC_2$ content detection model according to the optimal mixed sample; and using the Cd—$PC_2$ content detection model to determine a cadmium chelate content in a to-be-tested plant. The present disclosure can quickly and in-situ detect the heavy metal accumulation capacity of a plant.

10 Claims, 6 Drawing Sheets

METHOD AND SYSTEM FOR IN-SITU DETECTION OF CADMIUM CHELATES IN PLANTS

FIELD OF THE INVENTION

The present disclosure relates to the field of cadmium chelate detection, and in particular to a method and system for the in-situ detection of cadmium chelates in a plant.

BACKGROUND OF THE INVENTION

Due to human activities, lots of heavy metal elements enter the soil system, causing heavy metal pollution. Cadmium pollution is a relatively-common soil heavy metal pollution, which has become a major environmental problem that endangers human health due to the migration of cadmium in the soil-plant-food chain system.

The traditional physical and chemical treatment methods for heavy metal pollution (such as earth filling, soil washing, and electrochemical methods) can achieve prominent treatment effects, but have disadvantages such as high cost, difficult management, frequent secondary pollution, and large environmental disturbance. At the end of the last century, Chaney first proposed a phytoremediation method where the content of heavy metals in soil is reduced by growing plants capable of absorbing heavy metals in large quantities. Phytoremediation shows little disturbance to a soil environment, low cost, and no secondary pollution, and can achieve permanent in-situ remediation. Therefore, phytoremediation has become a research hotspot of soil remediation technology. Some acknowledged accumulators such as *Brassica junica* grow rapidly, have large biomasses, and can transfer more than 88% of absorbed heavy metals to aboveground parts, thus achieving extremely-high soil purification rates.

However, in practical applications, phytoremediation also has some shortcomings. For example, in some growth environments, an accumulator has low biomass, slow growth, and underdeveloped root systems, which cannot achieve effective accumulation at low heavy metal concentrations, but presents inhibited growth at high heavy metal concentrations, thus reducing the efficiency and environmental applicability of phytoremediation. It can be known that the key to the efficiency of phytoremediation is the adaptability of accumulator varieties to application environments and the accumulation and tolerance of accumulator varieties to heavy metals in the soil. It is a new direction for research of phytoremediation technology to integrate fast-growing, high-biomass, and adaptable varieties with the domestication and hybridization techniques to obtain practically-valuable hyperaccumulator varieties.

Hyperaccumulators are varieties with a heavy metal accumulation capacity 100 times that of ordinary plant varieties. At present, at least 400 species of plants in 45 families have been identified as hyperaccumulators, mainly concentrated in *Brassica, Alyssuns*, and *Thlaspi* of the cruciferous family, and most germplasms are distributed abroad. *Brassica chinensis* is one of the main cruciferous crops in China, some varieties of which also have a strong Cd accumulation ability. Studying, cultivating and improving heavy metal hyperaccumulation *Brassica chinensis* varieties with independent intellectual property rights and a Cd accumulation capacity thereof is significant for the accumulation of technologies in the field of soil heavy metal phytoremediation, hyperaccumulator germplasm resources, and new variety development technologies in China.

Calculation of many indexes (transfer coefficient, accumulation coefficient, etc.) traditionally used to measure the heavy metal accumulation capacity of a plant is based on a heavy metal content in each part of the plant, and the tolerance can only be indirectly reflected by a degree to which the plant phenotype or quality is inhibited (such as a root-shoot ratio). However, the heavy metal tolerance of some plants is manifested as the excretion of heavy metals through mechanisms such as excretion or senescence, for example, some abscisic acids (ABAs) are secreted to promote the abscission of poisoned leaves. Therefore, plants with strong heavy metal tolerance do not necessarily have strong heavy metal accumulation capacity at the same time, and may not have the function of phytoremediation. In addition, a plant itself synthesizes several small molecular compound ligands to chelate with heavy metal ions to form less toxic complexes, which are then transferred and fixed to a specific area in cells for isolation. Such small molecules include metallothioneins (MTs), organic acids, amino acids, etc. Phytochelatins (PCs, ($\gamma$-Glu-Cys)n-X, n=2 to 11, X may be absent or may be Gly, $\beta$-Ala, Ser, Glu, etc.) are a group of cysteine-rich polypeptides, which belong to the Class III MTs that are ubiquitous in plants and the most important in heavy metal resistance. PC chelates with a heavy metal ion via mercapto on cysteine to form a non-toxic heavy metal-S chelate. Therefore, a heavy metal-S bond can be used to distinguish between free and complex heavy metals, and a content thereof can be used as an important index for simultaneously characterizing the heavy metal accumulation and tolerance of a plant. Hyperaccumulators capable of synthesizing more chelates can be regarded as having both superior heavy metal adsorption capacity and superior heavy metal tolerance. Such hyperaccumulators are identified for selective breeding to obtain new varieties with further-enhanced phytoremediation performance.

At present, there are few studies on the detection and structure analysis methods of heavy metal chelates. Existing methods generally adopt separation by SEC-HPLC first and then determination by ICP-MS, and the lengthy process and the organic mobile phases and derivatization reagents used will result in damage to a biomass structure, thereby affecting the accuracy of detection results. Moreover, existing near-infrared, Raman and other spectroscopic in-situ rapid detection methods are limited at low resolution, and a sample needs to be crushed uniformly before detection. Research on the characteristic spectral information of a chelate still stagnates at the level of semi-empirical computer simulation. Therefore, it is impossible to quickly detect chelate formation in-situ at present. The potential hyperaccumulation ability of a plant can only be identified by detecting the sequences and expressions of two currently-known genes related to the regulation of accumulation traits, which is costly and labor-consuming.

Calculation of various classic indexes (accumulation coefficient, transfer coefficient, etc.) to measure phytoremediation performance is based on a heavy metal content in each part of a plant, and the heavy metal tolerance can only be indirectly reflected by various classic plant phenotype indexes (dry weight, root-shoot ratio, etc.). Therefore, the overall evaluation process is cumbersome due to many indexes involved. Studies on the binding ratio of heavy metals with MTs and on the molecular structure of chelates also still stagnate at the level of computer simulation. Therefore, it is not yet possible to quickly detect chelate formation in-situ to comprehensively evaluate the heavy metal accumulation and tolerance of a variety.

Therefore, developing a method for rapid in-situ detection of the heavy metal accumulation capacity of a plant and for rapid identification of a variety with potential hyperaccumulation is of great significance for the technical reserves in the field of soil heavy metal phytoremediation in China.

SUMMARY OF THE INVENTION

The present disclosure is intended to provide a method and system for the in-situ detection of cadmium chelates in a plant, which can quickly and in-situ detect the cadmium accumulation capacity of a plant and thus can accurately and quickly evaluate the phytoremediation performance.

To achieve the above purpose, the present disclosure provides the following technical solutions.

A method for the in-situ detection of cadmium chelates in a plant includes:

preparing cadmium chloride samples with different concentrations and phytochelatin (PC) 2 samples with different concentrations;

using terahertz time-domain spectroscopy (THz-TDS) to determine a terahertz (THz) reflection image for the cadmium chloride samples and the PC 2 samples;

building a cadmium chloride content detection model according to first spectral data of the THz reflection images of the cadmium chloride samples;

building a PC 2 content detection model according to second spectral data of the THz reflection images of the PC 2 samples;

determining an optimal mixed sample according to the cadmium chloride content detection model and the PC 2 content detection model, where, the optimal mixed sample is a mixed sample of a cadmium chloride sample and a PC 2 sample and has the lowest cadmium chloride and PC 2 contents;

building a Cd—$PC_2$ content detection model according to the optimal mixed sample; and using the Cd—$PC_2$ content detection model to determine a cadmium chelate content in a to-be-tested plant.

Optionally, after the using THz-TDS to determine a THz reflection image for the cadmium chloride samples and the PC 2 samples, the method may further include:

subjecting spectral data in the THz reflection image of the cadmium chloride sample successively to noise signal elimination, scattering elimination, spectral baseline zeroing, and horizontal adjustment to obtain processed cadmium chloride spectral data;

subjecting spectral data in the THz reflection image of the PC 2 sample successively to noise signal elimination, scattering elimination, and horizontal adjustment to obtain processed PC 2 spectral data;

applying density-functional theory (DFT) to molecular structures of the cadmium chloride and PC 2 to determine effective spectral data for the cadmium chloride and PC 2;

screening the processed cadmium chloride spectral data using the effective cadmium chloride spectral data to obtain the first spectral data; and screening the processed PC 2 spectral data using the effective PC 2 spectral data to obtain the second spectral data.

Optionally, the building a cadmium chloride content detection model according to first spectral data of the THz reflection images of the cadmium chloride samples may specifically include:

dividing the first spectral data into a first modeling data set and a first correction data set;

according to the first modeling data set, using a partial least squares (PLS) regression algorithm to build a first regression model for the cadmium chloride;

according to the first modeling data set, using a principal component regression (PCR) algorithm to build a second regression model for the cadmium chloride;

using the first correction data set to determine a determination coefficient and a root-mean-square error (RMSE) for the first regression model and the second regression model, separately; and determining a regression model for the cadmium chloride with high determination coefficient and low RMSE as the cadmium chloride content detection model.

Optionally, the building a PC 2 content detection model according to second spectral data of the THz reflection images of the PC 2 samples may specifically include:

dividing the second spectral data into a second modeling data set and a second correction data set;

according to the second modeling data set, using a PLS regression algorithm to build a third regression model for the PC 2;

according to the second modeling data set, using a PCR algorithm to build a fourth regression model for the PC 2;

using the second correction data set to determine a determination coefficient and an RMSE for the third regression model and the fourth regression model, separately; and determining a regression model for the PC 2 with high determination coefficient and low RMSE as the PC 2 content detection model.

Optionally, the determining an optimal mixed sample according to the cadmium chloride content detection model and the PC 2 content detection model may specifically include:

preparing mixed samples in different mixing ratios;

using THz-TDS to determine a THz reflection image for the mixed samples;

screening spectral data in the THz reflection images of the mixed samples using the effective cadmium chloride spectral data and the effective PC 2 spectral data to obtain third spectral data;

according to the third spectral data, using the cadmium chloride content detection model and the PC 2 content detection model to determine contents of the cadmium chloride and PC 2; and determining a mixed sample with the lowest cadmium chloride and PC 2 contents as the optimal mixed sample.

A system for the in-situ detection of cadmium chelates in a plant includes:

a first preparation module configured to prepare cadmium chloride samples with different concentrations and PC 2 samples with different concentrations;

a THz reflection image determination module configured to use THz-TDS to determine a THz reflection image for the cadmium chloride samples and the PC 2 samples;

a cadmium chloride content detection model building module configured to build a cadmium chloride content detection model according to first spectral data of the THz reflection images of the cadmium chloride samples;

a PC 2 content detection model building module configured to build a PC 2 content detection model according to second spectral data of the THz reflection images of the PC 2 samples;

an optimal mixed sample determination module configured to determine an optimal mixed sample according to the cadmium chloride content detection model and the PC 2 content detection model, where, the optimal mixed sample is a mixed sample of a cadmium chloride sample and a PC 2 sample and has the lowest cadmium chloride and PC 2 contents;

a Cd—$PC_2$ content detection model building module configured to build a Cd—$PC_2$ content detection model according to the optimal mixed sample; and a cadmium chelate content determination module configured to use the Cd—$PC_2$ content detection model to determine a cadmium chelate content in a to-be-tested plant.

Optionally, the system for the in-situ detection of cadmium chelates in a plant may further include:

a first data processing module configured to subject spectral data in the THz reflection image of the cadmium chloride sample successively to noise signal elimination, scattering elimination, spectral baseline zeroing, and horizontal adjustment to obtain processed cadmium chloride spectral data;

a second data processing module configured to subject spectral data in the THz reflection image of the PC 2 sample successively to noise signal elimination, scattering elimination, and horizontal adjustment to obtain processed PC 2 spectral data;

an effective spectral data determination module configured to apply DFT to molecular structures of the cadmium chloride and PC 2 to determine effective spectral data for the cadmium chloride and PC 2;

a first spectral data determination module configured to screen the processed cadmium chloride spectral data using the effective cadmium chloride spectral data to obtain the first spectral data; and a second spectral data determination module configured to screen the processed PC 2 spectral data using the effective PC 2 spectral data to obtain the second spectral data.

Optionally, the cadmium chloride content detection model building module may specifically include:

a first data division unit configured to divide the first spectral data into a first modeling data set and a first correction data set;

a first regression model building unit configured to use a PLS regression algorithm to build a first regression model for the cadmium chloride according to the first modeling data set;

a second regression model building unit configured to use a PCR algorithm to build a second regression model for the cadmium chloride according to the first modeling data set;

a first index data determination unit configured to use the first correction data set to determine a determination coefficient and an RMSE for the first regression model and the second regression model, separately; and a cadmium chloride content detection model determination unit configured to determine a regression model for the cadmium chloride with high determination coefficient and low RMSE as the cadmium chloride content detection model.

Optionally, the PC 2 content detection model building module may specifically include:

a second data division unit configured to divide the second spectral data into a second modeling data set and a second correction data set;

a third regression model building unit configured to use a PLS regression algorithm to build a third regression model for the PC 2 according to the second modeling data set;

a fourth regression model building unit configured to use a PCR algorithm to build a fourth regression model for the PC 2 according to the second modeling data set;

a second index data determination unit configured to use the second correction data set to determine a determination coefficient and an RMSE for the third regression model and the fourth regression model, separately; and a PC 2 content detection model determination unit configured to determine a regression model for the PC 2 with high determination coefficient and low RMSE as the PC 2 content detection model.

Optionally, the optimal mixed sample determination module may specifically include:

a mixed sample preparation unit configured to prepare mixed samples in different mixing ratios;

a THz reflection image determination unit configured to use THz-TDS to determine a THz reflection image for the mixed samples;

a third spectral data determination unit configured to screen spectral data in the THz reflection images of the mixed samples using the effective cadmium chloride spectral data and the effective PC 2 spectral data to obtain third spectral data;

a cadmium chloride and PC 2 content determination unit configured to use the cadmium chloride content detection model and the PC 2 content detection model to determine contents of the cadmium chloride and PC 2 according to the third spectral data; and an optimal mixed sample determination unit configured to determine a mixed sample with the lowest cadmium chloride and PC 2 contents as the optimal mixed sample.

According to specific examples provided in the present disclosure, the present disclosure discloses the following technical effects:

In the method and system for the in-situ detection of cadmium chelates in a plant according to the present disclosure, terahertz time-domain spectroscopy (THz-TDS) is used to determine terahertz (THz) reflection images of $CdCl_2$ and PC 2 samples; first spectral data of the THz reflection images of cadmium chloride samples are used to build a cadmium chloride content detection model, and second spectral data of the THz reflection images of the PC 2 samples are used to build a PC 2 content detection model; a mixed sample with the lowest $CdCl_2$ and PC 2 contents is determined as an optimal mixed sample according to spectral data of mixed samples obtained by mixing $CdCl_2$ and PC 2 samples in different ratios; the optimal mixed sample is used to build a Cd—$PC_2$ content detection model; and the Cd—$PC_2$ content detection model is used to determine a cadmium chelate content in a to-be-tested plant, thus realizing the rapid in-situ detection of a chelated Cd content in different varieties of *Brassica chinensis*. Moreover, the present disclosure can accurately and quickly evaluate the phytoremediation performance of a plant by simultaneously characterizing the heavy metal accumulation capacity and heavy metal tolerance of the plant.

BRIEF DESCRIPTION OF THE DRAWINGS

To describe the technical solutions in the examples of the present disclosure or in the prior art more clearly, the following briefly introduces the accompanying drawings required for describing the examples. Apparently, the accompanying drawings in the following description show merely some examples of the present disclosure, and a person of ordinary skill in the art may still derive other drawings from these accompanying drawings without creative efforts.

DETAILED DESCRIPTION OF THE INVENTION

The technical solutions in the examples of the present disclosure are clearly and completely described below with reference to the accompanying drawings in the examples of the present disclosure. Apparently, the described examples are merely a part rather than all of the examples of the present disclosure. All other examples obtained by a person of ordinary skill in the art based on the examples of the present disclosure without creative efforts shall fall within the protection scope of the present disclosure.

The present disclosure is intended to provide a method and system for the in-situ detection of cadmium chelates in a plant, which can quickly and in-situ detect the heavy metal accumulation capacity of a plant and thus can accurately and quickly evaluate the phytoremediation performance.

To make the foregoing objectives, features, and advantages of the present disclosure more comprehensible, the present disclosure is further described in detail below with reference to the accompanying drawings and specific implementations.

Figure 1:
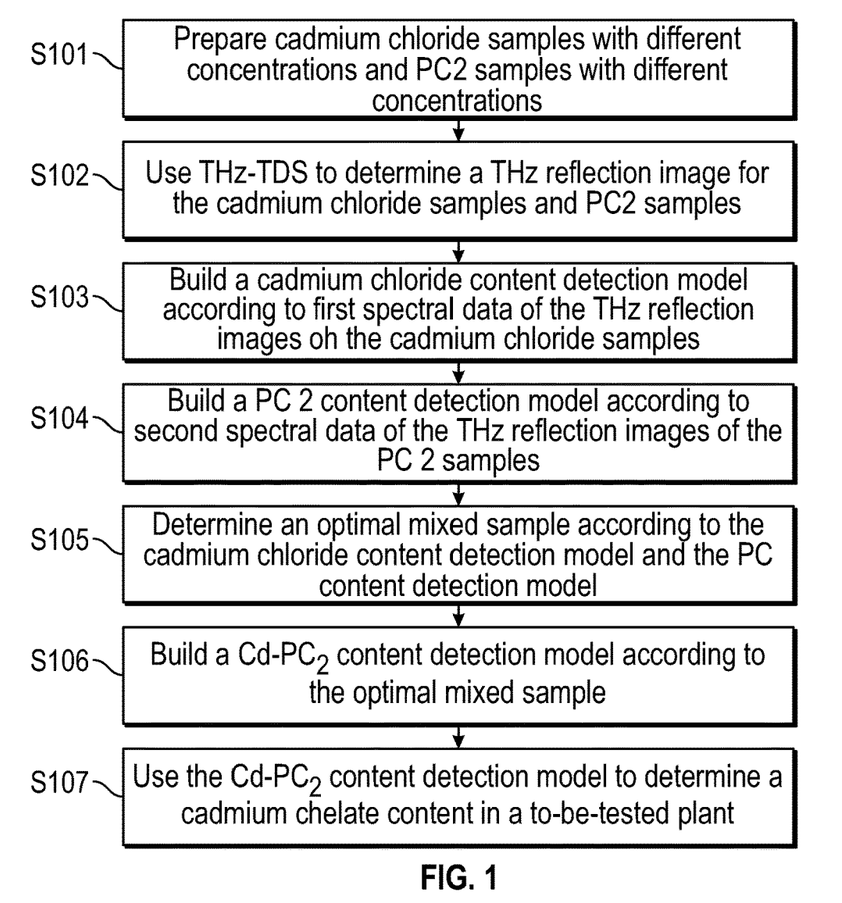
FIG. 1 is a schematic flow chart of the method for the in-situ detection of cadmium chelates in a plant according to the present disclosure.

FIG. 1 is a schematic flow chart of the method for the in-situ detection of cadmium chelates in a plant according to the present disclosure. As shown in FIG. 1, the method for the in-situ detection of cadmium chelates in a plant according to the present disclosure includes the following steps.

S101: Cadmium chloride samples with different concentrations and PC 2 samples with different concentrations were prepared.

A specific process for preparing samples was as follows:

1. 0.15 mg of $CdCl_2$ and 0.5 mg of $PC_2$ were taken and separately diluted with deionized water to obtain an 8× (8× represents 8-fold dilution, and it can be similarly understood below) standard sample solution with a concentration of $3.71 \times 10^{-5}$ mmol/ul.

2. Each of the two obtained 8× standard sample solutions was further diluted with deionized water to obtain 6×, 4×, 2×, and 1× standard sample solutions.

3. A polyethylene (PE) film with a thickness of 0.1 mm was used to cover a sample carrier for reflection imaging of a THz-TDS system, then 1 ul of each of the above standard sample solutions was added dropwise onto the PE film, and the dropwise addition was repeated 15 times (namely, a total of 15 ul for each sample, and 1 ul each time).

4. The sample carrier was dried in an air dry oven at 30° C., and finally a sample solute trace with a diameter of less than 2.4 mm was formed.

S102: THz-TDS was used to determine a THz reflection image for the cadmium chloride samples and the PC 2 samples.

Specifically, the CCT-1800 TDS-THz system was used for scanning at 20° C. in a nitrogen environment (nitrogen content >90%), with a scanning step of 0.16 and a sample thickness of 0.2 mm.

In order to ensure the quality of an obtained image for a sample, an image file obtained from scanning was loaded into the analysis software TdsAnalyzer. After the samples with obvious defects were manually eliminated, an image area with 15×15 pixel (2.4×2.4 $mm^2$) at a sample trace was selected (selection position: a trace with the center of the droplet as a center that was formed after the sample carrier added with the sample was dried; the center of the droplet was taken as a center when the trace was selected), and the spectral data in the image within a THz range of 0 to 3 were exported. That is, abnormal samples were eliminated.

Figure 4:
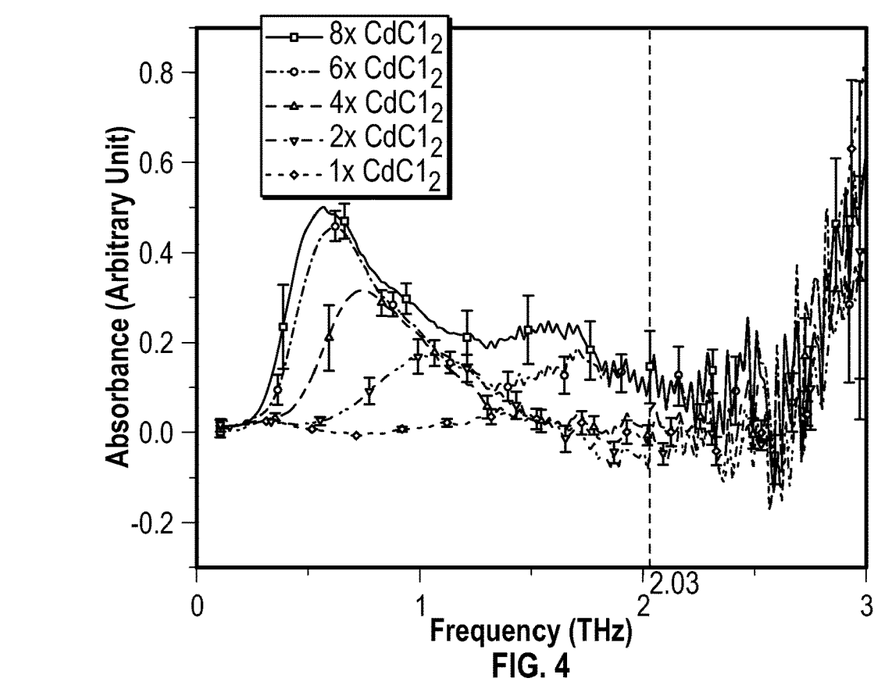
FIG. 4 shows the spectral data in the THz reflection images of the $CdCl_2$ samples according to the present disclosure.

After the S102, the method also includes the following:

Spectral data in the THz reflection image of the cadmium chloride sample were subjected successively to noise signal elimination, scattering elimination, spectral baseline zeroing, and horizontal adjustment to obtain processed cadmium chloride spectral data where the characteristic peaks were more significant and the noise was eliminated. The spectral data in the THz reflection image of the cadmium chloride sample were shown in FIG. 4.

Figure 6:
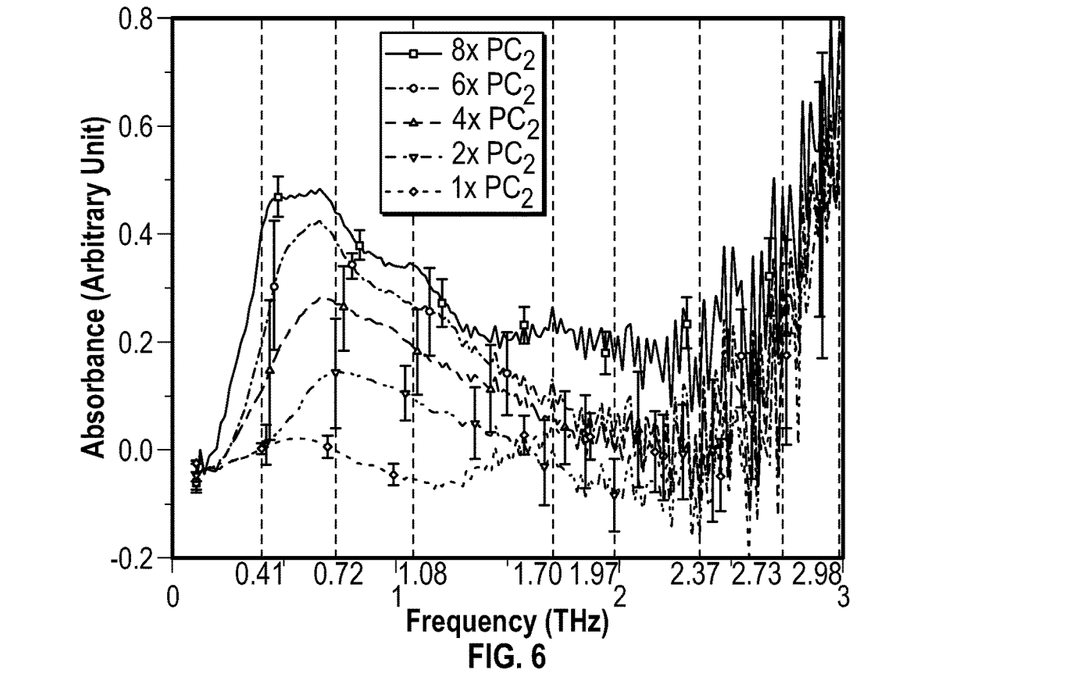
FIG. 6 shows the spectral data in the THz reflection images of the PC 2 samples according to the present disclosure.

Spectral data in the THz reflection image of the PC 2 sample were subjected successively to noise signal elimination, scattering elimination, and horizontal adjustment to obtain processed PC 2 spectral data where the characteristic peaks were more significant and the noise was eliminated. The spectral data in the THz reflection image of the PC 2 sample were shown in FIG. 6.

Density-functional theory (DFT) was applied to molecular structures of the cadmium chloride and PC 2 to determine effective spectral data for the cadmium chloride and PC 2. The effective spectral data of cadmium chloride and the effective spectral data of PC 2 were shown in FIG. 2 and FIG. 3, respectively.

Figure 2:
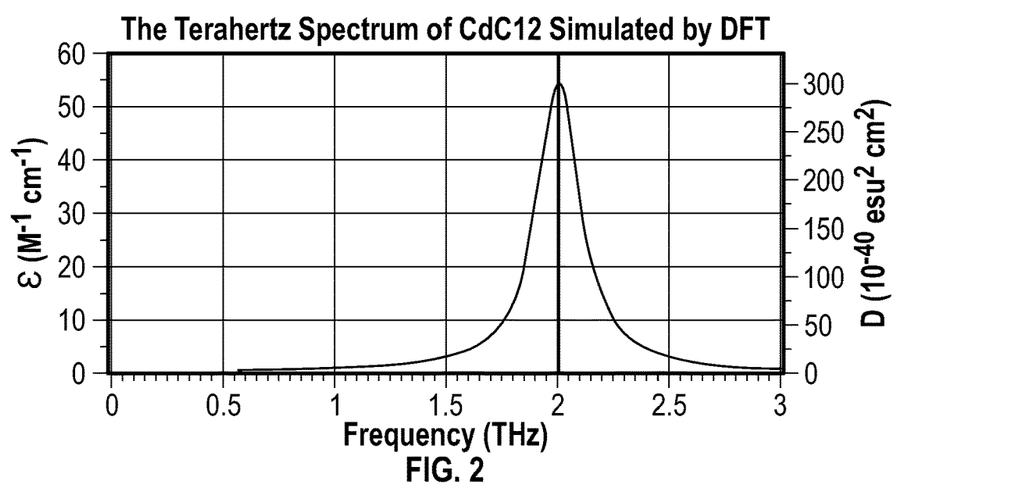
FIG. 2 is a schematic diagram of the THz band signal of $CdCl_2$ according to the present disclosure.
Figure 3:
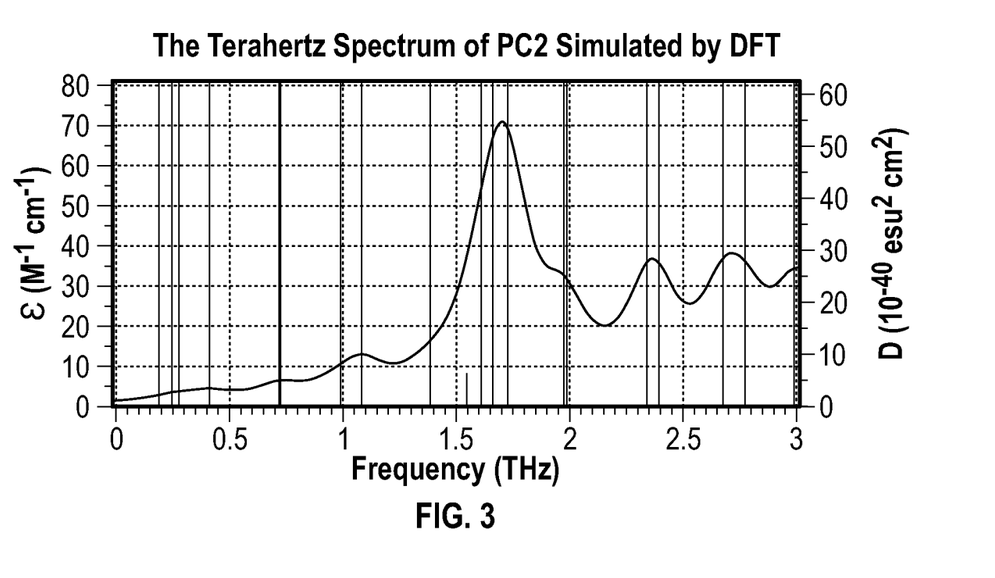
FIG. 3 is a schematic diagram of the THz band signal of PC 2 according to the present disclosure.

Specifically, according to known molecular structures of $PC_2$ and $CdCl_2$, the software Gaussview 6.0 was used to construct atomic space structures of the two molecules, and in the software Gaussian 16, the B3LYP/6-311+g(d,p) basis set of DFT was used to simulate the THz band signal of $PC_2$ and the pbepbe/lanl2dz basis set was used to simulate the THz band signal of $CdCl_2$.

The effective bands of the two were determined according to the distribution of characteristic peaks.

Figure 5:
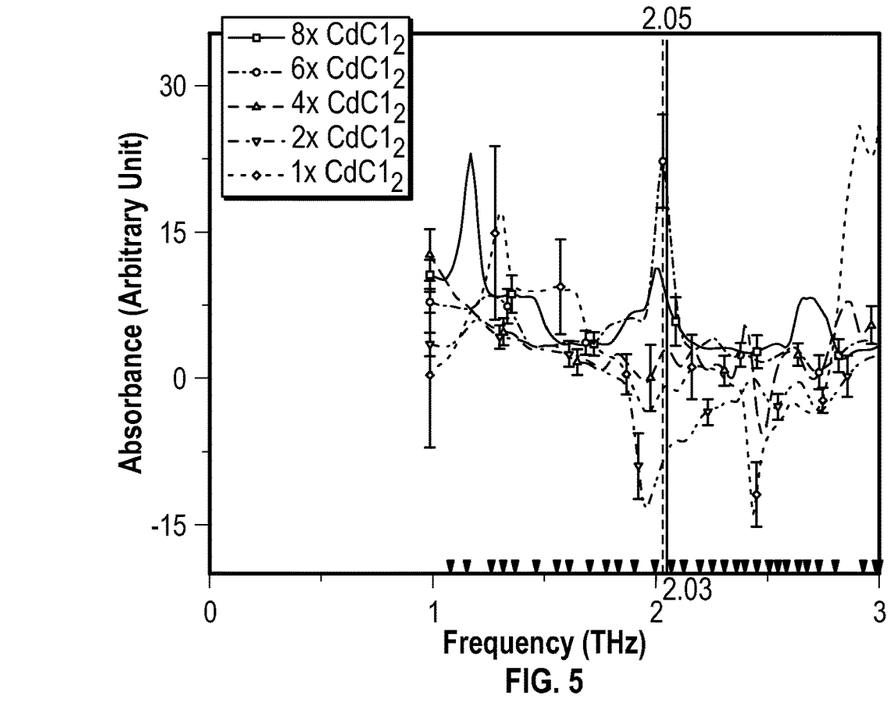
FIG. 5 shows the first spectral data of the $CdCl_2$ samples according to the present disclosure.

The processed cadmium chloride spectral data were screened using the effective cadmium chloride spectral data to obtain the first spectral data, as shown in FIG. 5.

Figure 7:
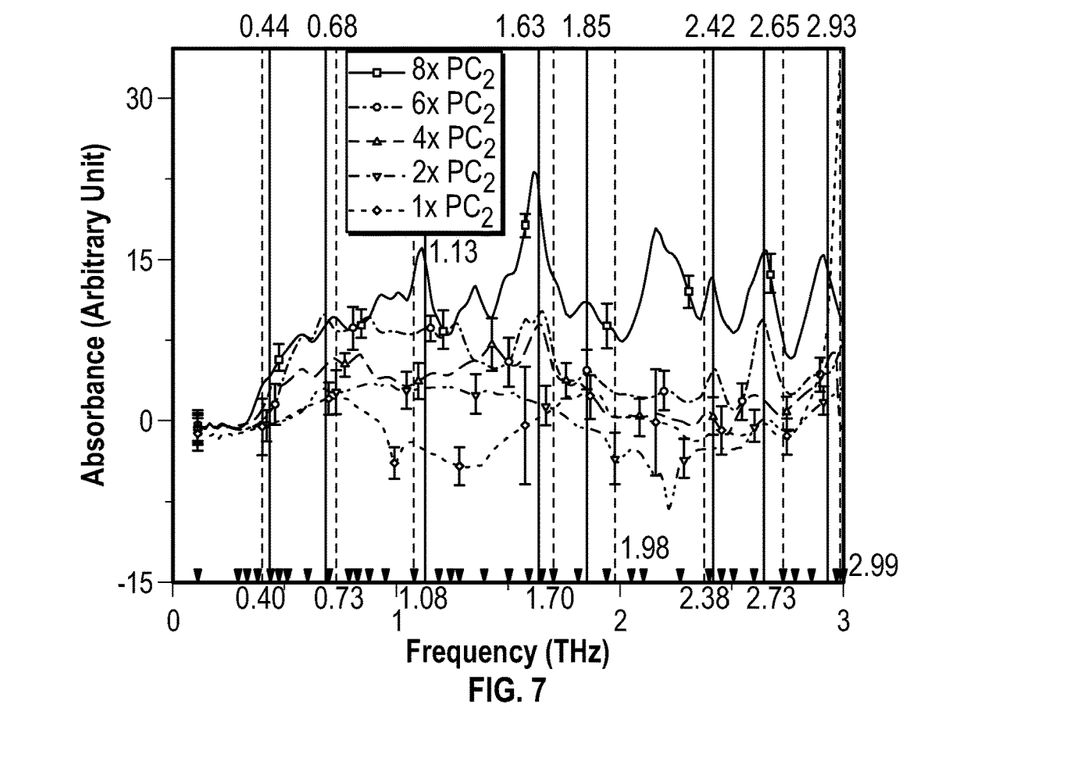
FIG. 7 shows the second spectral data of the PC 2 samples according to the present disclosure.

The processed PC 2 spectral data were screened using the effective PC 2 spectral data to obtain the second spectral data, as shown in FIG. 7.

As a specific example, based on the effective spectral data, the SPA algorithm was used to screen the processed cadmium chloride spectral data and the processed PC 2 spectral data, and 37 and 31 characteristic frequencies were screened out for the $PC_2$ and $CdCl_2$, respectively. Results were shown in Table 1 below.

TABLE 1

| Models for | SPA selected frequencies (THz) | | | | | | | | | | |
|---|---|---|---|---|---|---|---|---|---|---|---|
| CdCl$_2$ | 1.080 | 1.154 | 1.263 | 1.318 | 1.373 | 1.465 | 1.556 | 1.611 | 1.703 | 1.776 | 1.831 |
| | $x_1$ | $x_2$ | $x_3$ | $x_4$ | $x_5$ | $x_6$ | $x_7$ | $x_8$ | $x_9$ | $x_{10}$ | $x_{11}$ |
| | 1.904 | 1.996 | 2.069 | 2.124 | 2.197 | 2.252 | 2.307 | 2.362 | 2.399 | 2.454 | 2.509 |
| | $x_{12}$ | $x_{13}$ | $x_{14}$ | $x_{15}$ | $x_{16}$ | $x_{17}$ | $x_{18}$ | $x_{19}$ | $x_{20}$ | $x_{21}$ | $x_{22}$ |
| | 2.545 | 2.582 | 2.637 | 2.673 | 2.728 | 2.802 | 2.930 | 2.985 | 3.003 | | |
| | $x_{23}$ | $x_{24}$ | $x_{25}$ | $x_{26}$ | $x_{27}$ | $x_{28}$ | $x_{29}$ | $x_{30}$ | $x_{31}$ | | |
| PC$_2$ | 0.110 | 0.293 | 0.330 | 0.385 | 0.439 | 0.476 | 0.513 | 0.604 | 0.696 | 0.787 | 0.824 |
| | $x_1$ | $x_2$ | $x_3$ | $x_4$ | $x_5$ | $x_6$ | $x_7$ | $x_8$ | $x_9$ | $x_{10}$ | $x_{11}$ |
| | 0.879 | 0.952 | 1.080 | 1.190 | 1.245 | 1.282 | 1.392 | 1.501 | 1.593 | 1.648 | 1.703 |
| | $x_{12}$ | $x_{13}$ | $x_{14}$ | $x_{15}$ | $x_{16}$ | $x_{17}$ | $x_{18}$ | $x_{19}$ | $x_{20}$ | $x_{21}$ | $x_{22}$ |
| | 1.813 | 1.849 | 1.941 | 2.051 | 2.106 | 2.271 | 2.399 | 2.454 | 2.509 | 2.600 | 2.728 |
| | $x_{23}$ | $x_{24}$ | $x_{25}$ | $x_{26}$ | $x_{27}$ | $x_{28}$ | $x_{29}$ | $x_{30}$ | $x_{31}$ | $x_{32}$ | $x_{33}$ |
| | 2.783 | 2.856 | 2.966 | 3.003 | | | | | | | |
| | $x_{34}$ | $x_{35}$ | $x_{36}$ | $x_{37}$ | | | | | | | |
| Cd(PC$_2$)$_2$ | 0.110 | 0.128 | 0.165 | 0.220 | 0.275 | 0.366 | 0.421 | 0.513 | 0.549 | 0.623 | 0.732 |
| | $x_1$ | $x_2$ | $x_3$ | $x_4$ | $x_5$ | $x_6$ | $x_7$ | $x_8$ | $x_9$ | $x_{10}$ | $x_{11}$ |
| | 0.806 | 0.897 | 1.044 | 1.154 | 1.245 | 1.300 | 1.373 | 1.447 | 1.501 | 1.593 | 1.648 |
| | $x_{12}$ | $x_{13}$ | $x_{14}$ | $x_{15}$ | $x_{16}$ | $x_{17}$ | $x_{18}$ | $x_{19}$ | $x_{20}$ | $x_{21}$ | $x_{22}$ |
| | 1.685 | 1.721 | 1.776 | 1.831 | 1.886 | 1.923 | 1.996 | 2.032 | 2.087 | 2.142 | 2.216 |
| | $x_{23}$ | $x_{24}$ | $x_{25}$ | $x_{26}$ | $x_{27}$ | $x_{28}$ | $x_{29}$ | $x_{30}$ | $x_{31}$ | $x_{32}$ | $x_{33}$ |
| | 2.271 | 2.344 | 2.399 | 2.490 | 2.545 | 2.582 | 2.618 | 2.673 | 2.728 | 2.783 | 2.820 |
| | $x_{34}$ | $x_{35}$ | $x_{36}$ | $x_{37}$ | $x_{38}$ | $x_{39}$ | $x_{40}$ | $x_{41}$ | $x_{42}$ | $x_{43}$ | $x_{44}$ |
| | 2.875 | 2.948 | 2.985 | 3.003 | | | | | | | |
| | $x_{45}$ | $x_{46}$ | $x_{47}$ | $x_{48}$ | | | | | | | |

S103: A cadmium chloride content detection model was built according to first spectral data of the THz reflection images of the cadmium chloride samples. The following formula was used for determination:

$$f(x_n)=0.0108x_1+0.0160x_2+0.0174x_3+0.0078x_4+ \\ 0.0064x_5+0.0117x_6+0.0167x_7+0.0323x_8+ \\ 0.0302x_9+0.0622x_{10}+0.0390x_{11}+0.0203x_{12}+ \\ 0.0140x_{13}+0.0079x_{14}+0.0071x_{15}+0.0087x_{16}- \\ 0.0093x_{17}+0.0105x_{18}+0.0454x_{19}+0.0424x_{20}+ \\ 0.0388x_{21}+0.0325x_{22}+0.0319x_{23}+0.0248x_{24}+ \\ 0.0235x_{25}+0.0107x_{26}-0.0071x_{27}+0.0089x_{28}- \\ 0.0146x_{29}+0.0225x_{30}+0.0301x_{31}$$

A matrix $M[A(f_0), \ldots A(f_n),X]$ was defined, where, X represents a dilution factor of a standard sample solution, $f_n$ represents a characteristic frequency point obtained by SPA screening, and $A(f_n)$ represents an absorption intensity corresponding to a characteristic frequency point screened out.

The characteristic frequencies of PC$_2$ screened out by the SPA algorithm above were substituted into the defined matrix to obtain a concentration and characteristic frequency-specific matrix $M_{PC}$ for PC$_2$.

The characteristic frequencies of CdCL$_2$ screened out by the SPA algorithm above were substituted into the defined matrix to obtain a concentration and characteristic frequency-specific matrix $M_{Cd}$ for CdCL$_2$.

Moreover, the number of each of the two kinds of matrices was set to 50, with 10 for each concentration.

100 matrices were established in total.

S103 specifically includes the following:

The first spectral data were divided into a first modeling data set and a first correction data set.

According to the first modeling data set, a partial least squares (PLS) regression algorithm was used to build a first regression model for the cadmium chloride.

According to the first modeling data set, a principal component regression (PCR) algorithm was used to build a second regression model for the cadmium chloride.

The first correction data set was used to determine a determination coefficient and a root-mean-square error (RMSE) for the first regression model and the second regression model, separately.

A regression model for the cadmium chloride with high determination coefficient and low RMSE was determined as the cadmium chloride content detection model.

S104: A PC 2 content detection model was built according to second spectral data of the THz reflection images of the PC 2 samples. The following formula was used for determination:

$$f(x_n)=0.0065x_1+0.0070x_2+0.0201x_3+0.0312x_4+ \\ 0.0279x_5+0.0196x_6+0.0222x_7+0.0255x_8+ \\ 0.0308x_9+0.0196x_{10}+0.0242x_{11}+0.0244x_{12}+ \\ 0.0191x_{13}+0.0371x_{14}+0.0082x_{15}+0.0071x_{16}+ \\ 0.0042x_{17}+0.0217x_{18}+0.0293x_{19}-0.0021x_{20}+ \\ 0.0041x_{21}+0.0111x_{22}+0.0159x_{23}+0.0164x_{24}+ \\ 0.0057x_{25}+0.0228x_{26}+0.0028x_{27}+0.0247x_{28}+ \\ 0.0146x_{29}+0.0431x_{30}+0.0323x_{31}+0.0176x_{32}- \\ 0.0009x_{33}-0.0039x_{34}+0.0058x_{35}-0.0106x_{36}+ \\ 0.0142x_{37}$$

S104 specifically includes the following:

The second spectral data were divided into a second modeling data set and a second correction data set.

According to the second modeling data set, a PLS regression algorithm was used to build a third regression model for the PC 2.

According to the second modeling data set, a PCR algorithm was used to build a fourth regression model for the PC 2.

The second correction data set was used to determine a determination coefficient and an RMSE for the third regression model and the fourth regression model, separately.

A regression model for the PC 2 with high determination coefficient and low RMSE was determined as the PC 2 content detection model.

The performance of the detection models built by different methods was shown in Table 2 below.

TABLE 2

| Target detected by models | Spectral processing | Frequency selecting method/ number of frequencies | Modeling method[a] | Modeling set $R_C^2$ | Modeling set $RMSE_C$ | Prediction set $R_P^2$ | Prediction set $RMSE_P$ |
|---|---|---|---|---|---|---|---|
| $PC_2$ | Deresolve level-4 + MSC + BO + QN + GFS level-5 + HA | 0.1-3.0 THz full spectrum/159 SPA/37 | PLSR (I) | 0.9827 | 0.3300 | 0.9771 | 0.3977 |
|  |  |  | PCR (II) | 0.9525 | 0.5462 | 0.9505 | 0.5700 |
|  |  |  | PLSR (III) | 0.9859 (+0.32%) | 0.2972 (−9.94%) | 0.9791 (+0.20%) | 0.3745 (+5.83%) |
|  |  |  | PCR (IV) | 0.9634 (+1.14%) | 0.4794 (−12.23%) | 0.9637 (+1.39%) | 0.4938 (+13.37%) |
| $CdCl_2$ | Deresolve level-4 + MSC + QN + GFS level-5 + HA | 0.1-3.0 THz full spectrum/159 SPA/31 | PLSR (V) | 0.9803 | 0.3512 | 0.9674 | 0.4497 |
|  |  |  | PCR (VI) | 0.9821 | 0.3352 | 0.9646 | 0.4877 |
|  |  |  | PLSR (VII) | 0.9833 (+0.31%) | 0.3243 (−7.66%) | 0.9730 (+0.58%) | 0.4278 (−4.87%) |
|  |  |  | PCR (VIII) | 0.9542 (−2.84%) | 0.5366 (+60.08%) | 0.9470 (−1.82%) | 0.5878 (+20.52%) |
| $Cd(PC_2)_2$ | Deresolve level-4 + QN + GFS level-5 + HA | 0.1-3.0 THz full spectrum/159 SPA/48 | PLSR (IX) | 0.9656 | 0.4750 | 0.9456 | 0.6236 |
|  |  |  | PCR (X) | 0.9669 | 0.4662 | 0.9513 | 0.5671 |
|  |  |  | PLSR (XI) | 0.9741 (+0.88%) | 0.4125 (−13.16%) | 0.9513 (+0.60%) | 0.5769 (−7.49%) |
|  |  |  | PCR (XII) | 0.9523 (−1.51%) | 0.5595 (+20.01%) | 0.9186 (−3.44%) | 0.7544 (+33.03%) |

S105: An optimal mixed sample was determined according to the cadmium chloride content detection model and the PC 2 content detection model. The optimal mixed sample was a mixed sample of a cadmium chloride sample and a PC 2 sample and has the lowest cadmium chloride and PC 2 contents.

S105 specifically includes the following:

Mixed samples in different mixing ratios were prepared. 1.85 ul, 2.5 ul, 3.75 ul, 5.0 ul, and 15.0 ul of the 8× standard sample solution of $CdCl_2$ each were to 7.5 ul of the 8× standard sample solution of $PC_2$ to obtain standard mixed sample solutions where the two solutes had a ratio of 4:1, 3:1, 2:1, 1:1, and 1:2, respectively.

THz-TDS was used to determine a THz reflection image for the mixed samples.

Spectral data in the THz reflection images of the mixed samples were screened using the effective cadmium chloride spectral data and the effective PC 2 spectral data to obtain third spectral data.

According to the third spectral data, the cadmium chloride content detection model and the PC 2 content detection model were used to determine contents of the cadmium chloride and PC 2.

A mixed sample with the lowest cadmium chloride and PC 2 contents was determined as the optimal mixed sample.

Figure 8:
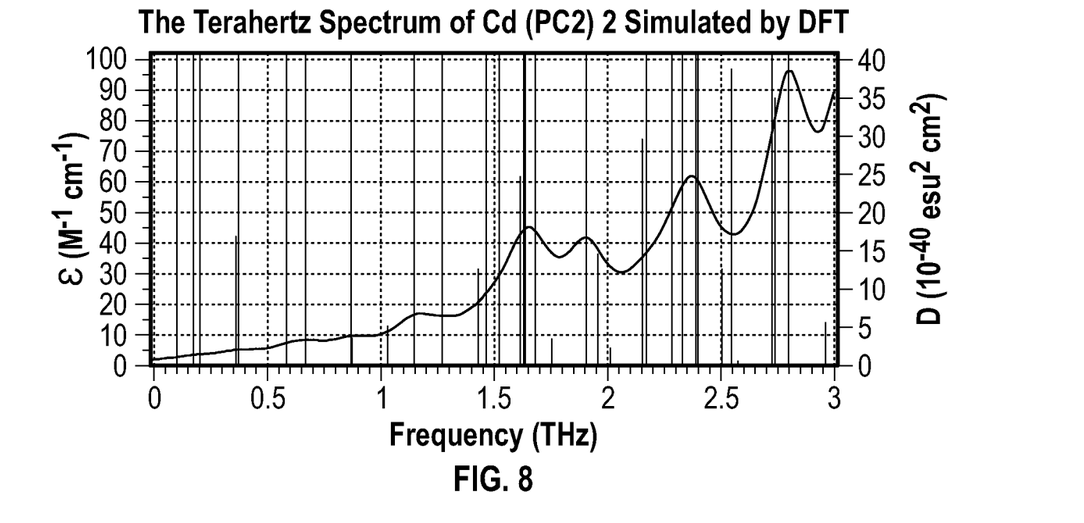
FIG. 8 is a schematic diagram of the THz band signal of $Cd(PC_2)_2$ according to the present disclosure.
Figure 9:
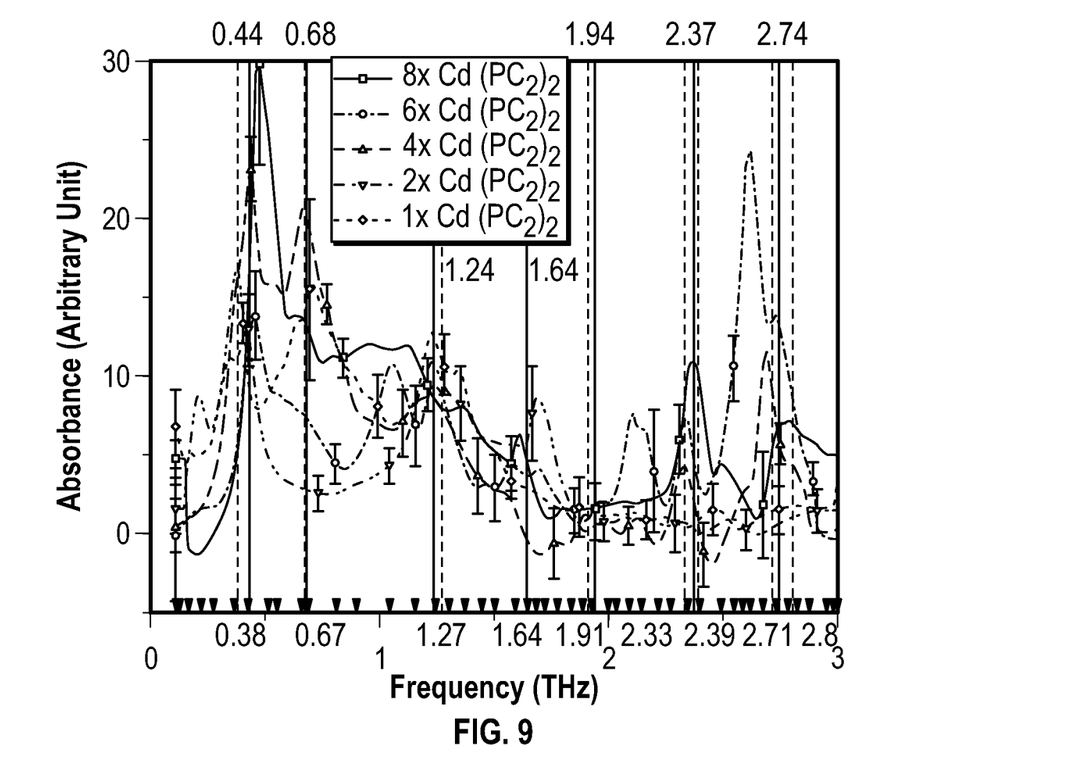
FIG. 9 shows the spectral data in the THz reflection images of the $Cd(PC_2)_2$ according to the present disclosure.

After the ratio of $PC_2:CdCl_2=2:1$ was determined, the pbepbe/lanl2dz basis set of DFT was used again to simulate the effective data of $Cd(PC_2)_2$. The characteristic peaks of the simulation results were highly consistent with the characteristic peaks of the actual scanning results, indicating that the actual scanning results were real and effective, as shown in FIG. 8 and FIG. 9.

S106: A Cd—$PC_2$ content detection model was built according to the optimal mixed sample. The following formula was used for determination:

$f(x_n) = -0.0652x_1 - 0.0645x_2 - 0.0341x_3 - 0.0636x_4 - 0.0159x_5 - 0.0338x_6 + 0.1240x_7 + 0.0683x_8 + 0.0329x_9 - 0.0133x_{10} - 0.1007x_{11} - 0.0294x_{12} + 0.0142x_{13} + 0.0610x_{14} + 0.0353x_{15} - 0.0484x_{16} - 0.0065x_{17} - 0.0127x_{18} + 0.0204x_{19} + 0.0086x_{20} + 0.0156x_{21} + 0.0159x_{22} + 0.0042x_{23} + 0.0039x_{24} - 0.0317x_{25} - 0.0449x_{26} - 0.0357x_{27} - 0.0274x_{28} - 0.0237x_{29} - 0.0252x_{30} - 0.0274x_{31} - 0.0292x_{32} - 0.0332x_{33} + 0.0339x_{34} - 0.0031x_{35} + 0.0004x_{36} - 0.0138x_{37} - 0.0219x_{38} - 0.0278x_{39} - 0.0164x_{40} + 0.0419x_{41} + 0.0583x_{42} + 0.0448x_{43} + 0.0457x_{44} + 0.0319x_{45} + 0.0179x_{46} + 0.0098x_{47} + 0.0097x_{48}$

S107: The Cd—$PC_2$ content detection model was used to determine a cadmium chelate content in a to-be-tested plant.

Every 100 mg of $CdCl_2$ was uniformly dissolved in every 5 L of soil to form a $Cd^{2+}$ stress rhizosphere environment at 20 mg/L, and three different varieties of *Brassica chinensis* (You Donger, Shanghai Green, and Suzhou Green) were sown and cultivated in the soil. After the plants grew for 40 days, leaves were harvested. The leaves were dried in an air dry oven at 35° C. for 12 h and then fixed on a sample carrier for scanning to obtain THz spectra. The average spectral data of *Brassica chinensis* leaves of the same variety growing under the same growth conditions without $Cd^{2+}$ stress were used as the background spectrum. The average spectrum was subtracted from the spectrum of each pixel of a sample image to obtain independent variable data according to the characteristic frequencies of the $Cd(PC_2)_2$ chelate, and results were substituted into the Cd—$PC_2$ content detection model to calculate the dilution factor x of the chelate in each pixel and an average value of all pixels. A $Cd(PC_2)_2$ content in the leaves was calculated according to the formula $$C = X \times \frac{P}{15 \times 15} \times t.$$

A data matrix composed of the chelate dilution factor x and a pixel coordinate in each pixel was imported into the software Origin 2018, and a distribution image was reconstructed by contour mapping. C is a $Cd(PC_2)_2$ content in scanned leaves; X is a dilution factor of the $Cd(PC_2)_2$ chelate in each pixel of scanned leaves; P is the total pixels of a scanned area, and t is a constant, namely, the content of a chelate in its 1× standard sample solution.

Further, the phytoremediation performance of *Brassica chinensis* was evaluated based on a chelate content as follows: A classic evaluation method for phytoremediation performance: The classic vegetation indexes (plant height, stem thickness, and dry and fresh weights of leaves and roots) were measured on the day when a *Brassica chinensis* sample was harvested. A chemical method (LIBS, ICP-MS, etc., LIBS was adopted here) was used to determine a Cd concentration in leaves and roots, and the classic phytoremediation performance indexes were calculated (transfer coefficient, accumulation coefficient, and root-shoot ratio). PCR was conducted on the software SPSS 22.0 to obtain the comprehensive scores of the three varieties. A higher score indicates better performance. There may be no significant difference among different varieties in terms of the same index. Therefore, the classical evaluation method identifies differences among varieties through comprehensive scores obtained by PCR for various indexes, which involves cumbersome measurement processes and large calculation amount. In the same situation, there was a significant difference in terms of the chelate content. Therefore, a chelate content can be quickly determined by the method of the present disclosure, and the content can be used as an index for evaluating the phytoremediation performance of a variety to quickly identify differences among varieties.

Figure 10:
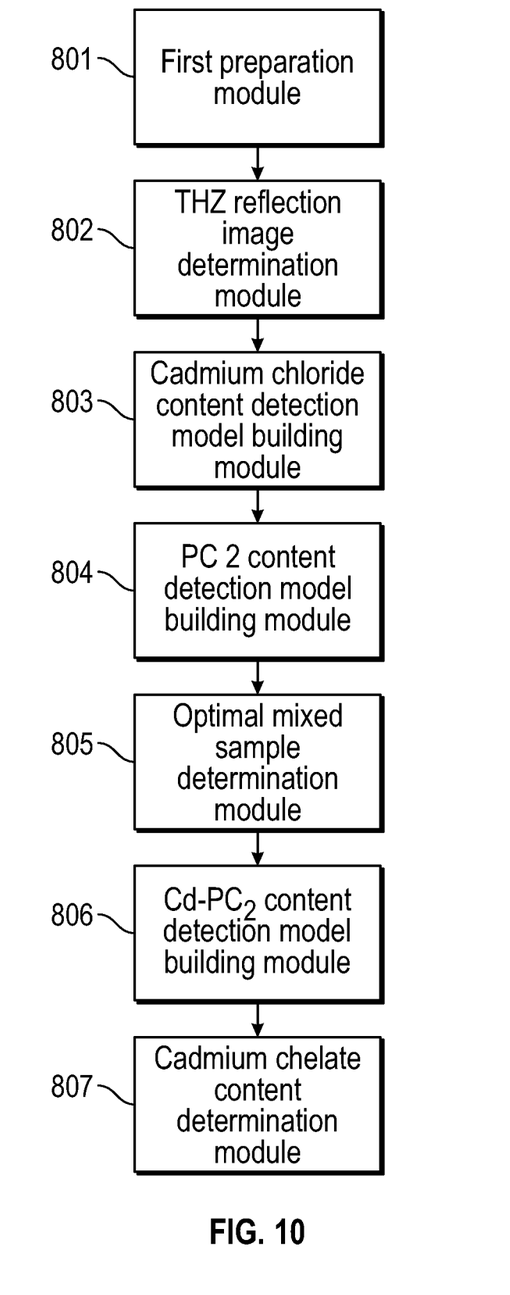
FIG. 10 is a structural diagram of the system for the in-situ detection of cadmium chelates in a plant according to the present disclosure.

FIG. 10 is a structural diagram of the system for the in-situ detection of cadmium chelates in a plant according to the present disclosure. As shown in FIG. 10, the system for the in-situ detection of cadmium chelates in a plant according to the present disclosure includes: a first preparation module 801, a THz reflection image determination module 802, a cadmium chloride content detection model building module 803, a PC 2 content detection model building module 804, an optimal mixed sample determination module 805, a Cd—$PC_2$ content detection model building module 806, and a cadmium chelate content determination module 807.

The first preparation module 801 is configured to prepare cadmium chloride samples with different concentrations and PC 2 samples with different concentrations.

The THz reflection image determination module 802 is configured to use THz-TDS to determine a THz reflection image for the cadmium chloride samples and the PC 2 samples.

The cadmium chloride content detection model building module 803 is configured to build a cadmium chloride content detection model according to first spectral data of the THz reflection images of the cadmium chloride samples.

The PC 2 content detection model building module 804 is configured to build a PC 2 content detection model according to second spectral data of the THz reflection images of the PC 2 samples.

The optimal mixed sample determination module 805 is configured to determine an optimal mixed sample according to the cadmium chloride content detection model and the PC 2 content detection model, where, the optimal mixed sample is a mixed sample of a cadmium chloride sample and a PC 2 sample and has the lowest cadmium chloride and PC 2 contents.

The Cd—$PC_2$ content detection model building module 806 is configured to build a Cd—$PC_2$ content detection model according to the optimal mixed sample.

The cadmium chelate content determination module 807 is configured to use the Cd—$PC_2$ content detection model to determine a cadmium chelate content in a to-be-tested plant.

The system for the in-situ detection of cadmium chelates in a plant according to the present disclosure may further include: a first data processing module, a second data processing module, an effective spectral data determination module, a first spectral data determination module, and a second spectral data determination module.

The first data processing module may be configured to subject spectral data in the THz reflection image of the cadmium chloride sample successively to noise signal elimination, scattering elimination, spectral baseline zeroing, and horizontal adjustment to obtain processed cadmium chloride spectral data.

The second data processing module may be configured to subject spectral data in the THz reflection image of the PC 2 sample successively to noise signal elimination, scattering elimination, and horizontal adjustment to obtain processed PC 2 spectral data.

The effective spectral data determination module may be configured to apply DFT to molecular structures of the cadmium chloride and PC 2 to determine effective spectral data for the cadmium chloride and PC 2.

The first spectral data determination module may be configured to screen the processed cadmium chloride spectral data using the effective cadmium chloride spectral data to obtain the first spectral data.

The second spectral data determination module may be configured to screen the processed PC 2 spectral data using the effective PC 2 spectral data to obtain the second spectral data.

The cadmium chloride content detection model building module 803 may specifically include: a first data division unit, a first regression model building unit, a second regression model building unit, a first index data determination unit, and a cadmium chloride content detection model determination unit.

The first data division unit may be configured to divide the first spectral data into a first modeling data set and a first correction data set.

The first regression model building unit may be configured to use a PLS regression algorithm to build a first regression model for the cadmium chloride according to the first modeling data set.

The second regression model building unit may be configured to use a PCR algorithm to build a second regression model for the cadmium chloride according to the first modeling data set.

The first index data determination unit may be configured to use the first correction data set to determine a determination coefficient and an RMSE for the first regression model and the second regression model, separately.

The cadmium chloride content detection model determination unit may be configured to determine a regression model for the cadmium chloride with high determination coefficient and low RMSE as the cadmium chloride content detection model.

The PC 2 content detection model building module 804 may specifically include: a second data division unit, a third regression model building unit, a fourth regression model building unit, a second index data determination unit, and a PC 2 content detection model determination unit.

The second data division unit may be configured to divide the second spectral data into a second modeling data set and a second correction data set.

The third regression model building unit may be configured to use a PLS regression algorithm to build a third regression model for the PC 2 according to the second modeling data set.

The fourth regression model building unit may be configured to use a PCR algorithm to build a fourth regression model for the PC 2 according to the second modeling data set.

The second index data determination unit may be configured to use the second correction data set to determine a determination coefficient and an RMSE for the third regression model and the fourth regression model, separately.

The PC 2 content detection model determination unit may be configured to determine a regression model for the PC 2 with high determination coefficient and low RMSE as the PC 2 content detection model.

The optimal mixed sample determination module 805 may specifically include: a mixed sample preparation unit, a THz reflection image determination unit, a third spectral data determination unit, a cadmium chloride and PC 2 content determination unit, and an optimal mixed sample determination unit.

The mixed sample preparation unit may be configured to prepare mixed samples in different mixing ratios.

The THz reflection image determination unit may be configured to use THz-TDS to determine a THz reflection image for the mixed samples.

The third spectral data determination unit may be configured to screen spectral data in the THz reflection images of the mixed samples using the effective cadmium chloride spectral data and the effective PC 2 spectral data to obtain third spectral data.

The cadmium chloride and PC 2 content determination unit may be configured to use the cadmium chloride content detection model and the PC 2 content detection model to determine contents of the cadmium chloride and PC 2 according to the third spectral data.

The optimal mixed sample determination unit may be configured to determine a mixed sample with the lowest cadmium chloride and PC 2 contents as the optimal mixed sample.

Each example of the present specification is described in a progressive manner, each example focuses on the difference from other examples, and the same and similar parts among the examples may refer to each other. For a system disclosed in the examples, since the system corresponds to the method disclosed in the examples, the description is relatively simple, and reference can be made to the method description.

Specific examples are used herein for illustration of the principles and implementations of the present disclosure. The description of the examples is used to help understand the method and its core principles of the present disclosure. In addition, those skilled in the art can make various modifications to the specific implementations and application scope in accordance with the teachings of the present disclosure. In conclusion, the content of the present specification shall not be construed as limiting the present disclosure.

What is claimed is:

1. A method for the in-situ detection of cadmium chelates in a plant, comprising:
    preparing cadmium chloride samples with different concentrations and phytochelatin (PC) 2 samples with different concentrations;
    using terahertz time-domain spectroscopy (THz-TDS) to determine a terahertz (THz) reflection image for the cadmium chloride samples and the PC 2 samples;
    building a cadmium chloride content detection model according to first spectral data of the THz reflection images of the cadmium chloride samples;
    building a PC 2 content detection model according to second spectral data of the THz reflection images of the PC 2 samples;
    determining an optimal mixed sample according to the cadmium chloride content detection model and the PC 2 content detection model, wherein, the optimal mixed sample is a mixed sample of a cadmium chloride sample and a PC 2 sample and has the lowest cadmium chloride and PC 2 contents;
    building a Cd—$PC_2$ content detection model according to the optimal mixed sample; and
    using the Cd—$PC_2$ content detection model to determine a cadmium chelate content in a to-be-tested plant; wherein
    the using the Cd—$PC_2$ content detection model to determine a cadmium chelate content in a to-be-tested plant specifically comprises:
    uniformly dissolving every 100 mg of $CdCl_2$ in every 5 L of soil to form a $Cd^{2+}$ stress rhizosphere environment at 20 mg/L, and sowing and cultivating three different varieties of *Brassica chinensis* (You Donger, Shanghai Green, and Suzhou Green) in the soil; after the plants grow for 40 days, harvesting leaves, drying the leaves in an air dry oven at 35° C. for 12 h and then fixing on a sample carrier for scanning to obtain THz spectra; using the average spectral data of *Brassica chinensis* leaves of the same variety growing under the same growth conditions without $Cd^{2+}$ stress as the background spectrum; subtracting the average spectrum from the spectrum of each pixel of a sample image to obtain independent variable data according to the characteristic frequencies of the $Cd(PC_2)_2$ chelate, and substituting results into the Cd—$PC_2$ content detection model to calculate the dilution factor x of the chelate in each pixel and an average value of all pixels; calculating a $Cd(PC_2)_2$ content in the leaves according to the formula $$C = X \times \frac{P}{15 \times 15} \times t;$$

importing a data matrix composed of the chelate dilution factor x and a pixel coordinate in each pixel into the software Origin 2018, and reconstructing a distribution image by contour mapping, wherein C is a $Cd(PC_2)_2$ content in scanned leaves; X is a dilution factor of the $Cd(PC_2)_2$ chelate in each pixel of scanned leaves; P is the total pixels of a scanned area, and t is a constant, namely, the content of a chelate in its 1× standard sample solution.

2. The method for the in-situ detection of cadmium chelates in a plant according to claim 1, wherein, after the using THz-TDS to determine a THz reflection image for the cadmium chloride samples and the PC 2 samples, the method further comprises:
    subjecting spectral data in the THz reflection image of the cadmium chloride sample successively to noise signal elimination, scattering elimination, spectral baseline zeroing, and horizontal adjustment to obtain processed cadmium chloride spectral data;
    subjecting spectral data in the THz reflection image of the PC 2 sample successively to noise signal elimination, scattering elimination, and horizontal adjustment to obtain processed PC 2 spectral data;
    applying density-functional theory (DFT) to molecular structures of the cadmium chloride and PC 2 to determine effective spectral data for the cadmium chloride and PC 2;
    screening the processed cadmium chloride spectral data using the effective cadmium chloride spectral data to obtain the first spectral data; and screening the processed PC 2 spectral data using the effective PC 2 spectral data to obtain the second spectral data.

3. The method for the in-situ detection of cadmium chelates in a plant according to claim 1, wherein, the building a cadmium chloride content detection model according to first spectral data of the THz reflection images of the cadmium chloride samples specifically comprises:
dividing the first spectral data into a first modeling data set and a first correction data set;
according to the first modeling data set, using a partial least squares (PLS) regression algorithm to build a first regression model for the cadmium chloride;
according to the first modeling data set, using a principal component regression (PCR) algorithm to build a second regression model for the cadmium chloride;
using the first correction data set to determine a determination coefficient and a root-mean-square error (RMSE) for the first regression model and the second regression model, separately; and
determining a regression model for the cadmium chloride with high determination coefficient and low RMSE as the cadmium chloride content detection model.

4. The method for the in-situ detection of cadmium chelates in a plant according to claim 1, wherein, the building a PC 2 content detection model according to second spectral data of the THz reflection images of the PC 2 samples specifically comprises:
dividing the second spectral data into a second modeling data set and a second correction data set;
according to the second modeling data set, using a PLS regression algorithm to build a third regression model for the PC 2;
according to the second modeling data set, using a PCR algorithm to build a fourth regression model for the PC 2;
using the second correction data set to determine a determination coefficient and an RMSE for the third regression model and the fourth regression model, separately; and
determining a regression model for the PC 2 with high determination coefficient and low RMSE as the PC 2 content detection model.

5. The method for the in-situ detection of cadmium chelates in a plant according to claim 2, wherein, the determining an optimal mixed sample according to the cadmium chloride content detection model and the PC 2 content detection model specifically comprises:
preparing mixed samples in different mixing ratios;
using THz-TDS to determine a THz reflection image for the mixed samples;
screening spectral data in the THz reflection images of the mixed samples using the effective cadmium chloride spectral data and the effective PC 2 spectral data to obtain third spectral data;
according to the third spectral data, using the cadmium chloride content detection model and the PC 2 content detection model to determine contents of the cadmium chloride and PC 2; and
determining a mixed sample with the lowest cadmium chloride and PC 2 contents as the optimal mixed sample.

6. A system for the in-situ detection of cadmium chelates in a plant, comprising:
a first preparation module configured to prepare cadmium chloride samples with different concentrations and PC 2 samples with different concentrations;
a THz reflection image determination module configured to use THz-TDS to determine a THz reflection image for the cadmium chloride samples and the PC 2 samples;
a cadmium chloride content detection model building module configured to build a cadmium chloride content detection model according to first spectral data of the THz reflection images of the cadmium chloride samples;
a PC 2 content detection model building module configured to build a PC 2 content detection model according to second spectral data of the THz reflection images of the PC 2 samples;
an optimal mixed sample determination module configured to determine an optimal mixed sample according to the cadmium chloride content detection model and the PC 2 content detection model, wherein, the optimal mixed sample is a mixed sample of a cadmium chloride sample and a PC 2 sample and has the lowest cadmium chloride and PC 2 contents;
a Cd—$PC_2$ content detection model building module configured to build a Cd—$PC_2$ content detection model according to the optimal mixed sample; and
a cadmium chelate content determination module configured to use the Cd—$PC_2$ content detection model to determine a cadmium chelate content in a to-be-tested plant; wherein
the using the Cd—$PC_2$ content detection model to determine a cadmium chelate content in a to-be-tested plant specifically comprises:
uniformly dissolving every 100 mg of $CdCl_2$ in every 5 L of soil to form a $Cd^{2+}$ stress rhizosphere environment at 20 mg/L, and sowing and cultivating three different varieties of *Brassica chinensis* (You Donger, Shanghai Green, and Suzhou Green) in the soil; after the plants grow for 40 days, harvesting leaves, drying the leaves in an air dry oven at 35° C. for 12 h and then fixing on a sample carrier for scanning to obtain THz spectra; using the average spectral data of *Brassica chinensis* leaves of the same variety growing under the same growth conditions without $Cd^{2+}$ stress as the background spectrum;
subtracting the average spectrum from the spectrum of each pixel of a sample image to obtain independent variable data according to the characteristic frequencies of the $Cd(PC_2)_2$ chelate, and substituting results into the Cd—$PC_2$ content detection model to calculate the dilution factor x of the chelate in each pixel and an average value of all pixels;
calculating a $Cd(PC_2)_2$ content in the leaves according to the formula $$C = X \times \frac{P}{15 \times 15} \times t;$$

importing a data matrix composed of the chelate dilution factor x and a pixel coordinate in each pixel into the software Origin 2018, and reconstructing a distribution image by contour mapping, wherein C is a $Cd(PC_2)_2$ content in scanned leaves; X is a dilution factor of the $Cd(PC_2)_2$ chelate in each pixel of scanned leaves; P is the total pixels of a scanned area, and t is a constant, namely, the content of a chelate in its 1× standard sample solution.

7. The system for the in-situ detection of cadmium chelates in a plant according to claim 6, further comprising:

a first data processing module configured to subject spectral data in the THz reflection image of the cadmium chloride sample successively to noise signal elimination, scattering elimination, spectral baseline zeroing, and horizontal adjustment to obtain processed cadmium chloride spectral data;

a second data processing module configured to subject spectral data in the THz reflection image of the PC 2 sample successively to noise signal elimination, scattering elimination, and horizontal adjustment to obtain processed PC 2 spectral data;

an effective spectral data determination module configured to apply DFT to molecular structures of the cadmium chloride and PC 2 to determine effective spectral data for the cadmium chloride and PC 2;

a first spectral data determination module configured to screen the processed cadmium chloride spectral data using the effective cadmium chloride spectral data to obtain the first spectral data; and a second spectral data determination module configured to screen the processed PC 2 spectral data using the effective PC 2 spectral data to obtain the second spectral data.

8. The system for the in-situ detection of cadmium chelates in a plant according to claim 6, wherein, the cadmium chloride content detection model building module specifically comprises:

a first data division unit configured to divide the first spectral data into a first modeling data set and a first correction data set;

a first regression model building unit configured to use a PLS regression algorithm to build a first regression model for the cadmium chloride according to the first modeling data set;

a second regression model building unit configured to use a PCR algorithm to build a second regression model for the cadmium chloride according to the first modeling data set;

a first index data determination unit configured to use the first correction data set to determine a determination coefficient and an RMSE for the first regression model and the second regression model, separately; and a cadmium chloride content detection model determination unit configured to determine a regression model for the cadmium chloride with high determination coefficient and low RMSE as the cadmium chloride content detection model.

9. The system for the in-situ detection of cadmium chelates in a plant according to claim 6, wherein, the PC 2 content detection model building module specifically comprises:

a second data division unit configured to divide the second spectral data into a second modeling data set and a second correction data set;

a third regression model building unit configured to use a PLS regression algorithm to build a third regression model for the PC 2 according to the second modeling data set;

a fourth regression model building unit configured to use a PCR algorithm to build a fourth regression model for the PC 2 according to the second modeling data set;

a second index data determination unit configured to use the second correction data set to determine a determination coefficient and an RMSE for the third regression model and the fourth regression model, separately; and a PC 2 content detection model determination unit configured to determine a regression model for the PC 2 with high determination coefficient and low RMSE as the PC 2 content detection model.

10. The system for the in-situ detection of cadmium chelates in a plant according to claim 7, wherein, the optimal mixed sample determination module specifically comprises:

a mixed sample preparation unit configured to prepare mixed samples in different mixing ratios;

a THz reflection image determination unit configured to use THz-TDS to determine a THz reflection image for the mixed samples;

a third spectral data determination unit configured to screen spectral data in the THz reflection images of the mixed samples using the effective cadmium chloride spectral data and the effective PC 2 spectral data to obtain third spectral data;

a cadmium chloride and PC 2 content determination unit configured to use the cadmium chloride content detection model and the PC 2 content detection model to determine contents of the cadmium chloride and PC 2 according to the third spectral data; and an optimal mixed sample determination unit configured to determine a mixed sample with the lowest cadmium chloride and PC 2 contents as the optimal mixed sample.

* * * * *